(12) United States Patent
Smith et al.

(10) Patent No.: US 10,856,877 B2
(45) Date of Patent: Dec. 8, 2020

(54) DETACHABLE IMPLANTABLE DEVICES

(71) Applicant: Boston Scientific Scimed, Inc., Maple Grove, MN (US)

(72) Inventors: Mark S. Smith, Coon Rapids, MN (US); James M. Anderson, Corcoran, MN (US); David Raab, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 393 days.

(21) Appl. No.: 15/206,253

(22) Filed: Jul. 9, 2016

(65) Prior Publication Data

US 2017/0007266 A1    Jan. 12, 2017

Related U.S. Application Data

(60) Provisional application No. 62/191,110, filed on Jul. 10, 2015.

(51) Int. Cl.
    *A61B 17/12*    (2006.01)

(52) U.S. Cl.
    CPC .... *A61B 17/12113* (2013.01); *A61B 17/1214* (2013.01); *A61B 2017/12054* (2013.01); *A61B 2017/12081* (2013.01)

(58) Field of Classification Search
    CPC ........ A61B 17/12022; A61B 17/12113; A61B 17/1214; A61B 2017/12054; A61B 2017/12081; A61B 17/12145; A61B 17/1215; A61B 17/12159; A61B 17/12163; A61B 17/12168; A61B 17/3468; A61N 2001/0578
    USPC .......................... 606/108, 191, 194, 198, 200
    See application file for complete search history.

(56) References Cited

U.S. PATENT DOCUMENTS

| | | | |
|---|---|---|---|
| 6,712,826 B2 * | 3/2004 | Lui | A61N 1/056 606/108 |
| 7,118,539 B2 * | 10/2006 | Vrba | A61M 25/09 600/585 |
| 10,076,336 B2 * | 9/2018 | Kleshinski | A61B 17/12031 |
| 2001/0002438 A1 | 5/2001 | Sepetka et al. | |
| 2002/0010475 A1 * | 1/2002 | Lui | A61N 1/057 606/108 |
| 2004/0015224 A1 | 1/2004 | Armstrong et al. | |
| 2004/0193178 A1 | 9/2004 | Nikolchev | |
| 2007/0299422 A1 | 12/2007 | Inganas et al. | |
| 2009/0221967 A1 * | 9/2009 | Thommen | A61B 17/22031 604/164.09 |
| 2014/0236214 A1 | 8/2014 | Goode et al. | |
| 2016/0008003 A1 * | 1/2016 | Kleshinski | A61B 17/12031 606/200 |
| 2016/0157869 A1 | 6/2016 | Elg rd et al. | |

FOREIGN PATENT DOCUMENTS

WO    WO 2014145012 A2 *   9/2014   ....... A61B 17/12031

* cited by examiner

*Primary Examiner* — Kathleen S Holwerda

(57) ABSTRACT

Described herein are delivery devices and systems for delivering a detachable medical device and various associated methods of using such devices and systems.

19 Claims, 2 Drawing Sheets

DETACHABLE IMPLANTABLE DEVICES

FIELD OF THE DISCLOSURE

The present disclosure relates, inter alia, to devices and systems for delivery devices and systems for delivering a detachable medical device and various associated methods of using such devices and systems.

BACKGROUND

The endovascular treatment of a variety of conditions throughout the body is an increasingly more important form of therapy. One such procedure uses embolization coils to occlude a target site by forming a physical barrier to blood flow and/or by promoting thrombus formation at the site. Such treatments can be useful where it is desired to reduce vascularization, including treatments for aneurisms and cancer.

Coils have typically been placed at the desired site within the vasculature using a catheter and a delivery device such as a pusher member. As a first step, a flexible, small diameter catheter can be guided to the target site through the use of a guidewire or by other means. Once the site has been reached, the catheter lumen is cleared by removing the guidewire (if a guidewire has been used), and the coil is placed into the proximal open end of the catheter and advanced through the catheter via the delivery device, which has a distal end that is adapted to engage and push the coil through the catheter lumen as the delivery device is advanced through the catheter. When the coil reaches the distal end of the catheter, it is discharged from the catheter by the delivery device into the vascular site.

Several techniques have been developed to enable more accurate placement of coils within a vessel, including techniques where the delivery device is temporarily affixed to the coil, and which can be released via electrical (e.g., electrolytic dissolution) and mechanical means (e.g., interlocking members operated by an activation wire).

The present disclosure pertains to improved devices, systems and methods for implantable device delivery.

SUMMARY

In some aspects, the present disclosure pertains to delivery devices for delivering detachable medical devices, the delivery devices comprising: (a) a first delivery mechanism comprising (i) a first elongate member having a first elongate member lumen and (ii) an expandable member having an expandable member lumen and a first lateral width when in a relaxed state, the expandable member being positioned distal to the first elongate member; and (b) a second delivery mechanism comprising (i) a second elongate member and (ii) an increased diameter member having a proximal facing surface, the increased diameter member being positioned distal to and mechanically coupled to the first elongate member. The second elongate member is at least partially positioned within the first elongate member lumen and the expandable member lumen, the second elongate member is axially moveable relative to the first elongate member lumen and the expandable member lumen, and the increased diameter member is positioned distal to the second elongate member such that when the second elongate member is pulled proximally relative to the first elongate member, the proximal facing surface of the increased diameter member engages the expandable member and expands the expandable member to an expanded state having a second lateral width that is greater than the first lateral width.

In some embodiments of the preceding aspects, the first elongate member may comprise a hollow cylindrical region having a lumen with a substantially circular cross-section.

In some embodiments, which may be used in conjunction with any of the preceding aspects and embodiments, the second elongate member may comprise a solid or hollow cylindrical region having a substantially circular cross-section.

In some embodiments, which may be used in conjunction with any of the preceding aspects and embodiments, the first elongate member may be mechanically coupled to the expandable member.

In some embodiments, which may be used in conjunction with any of the preceding aspects and embodiments, the second elongate member and the increased diameter member may be formed from different materials, or the second elongate member and the increased diameter member may be formed from the same material and are of a unitary construction.

In some embodiments, which may be used in conjunction with any of the preceding aspects and embodiments, when the increased diameter member is in an unexpanded state, the increased diameter member may have a width that is approximately equal to the first lateral width.

In some embodiments, which may be used in conjunction with any of the preceding aspects and embodiments, the increased diameter member may have substantially circular cross-section.

In some embodiments, which may be used in conjunction with any of the preceding aspects and embodiments, the proximal facing surface of the increased diameter member may be configured to engage the expandable member by moving at least partially axially into the expandable member lumen such that the expandable member is expanded to the expanded state.

In some embodiments, which may be used in conjunction with any of the preceding aspects and embodiments, the proximal facing surface of the increased diameter member may be a tapered surface.

In some embodiments, which may be used in conjunction with any of the preceding aspects and embodiments, the proximal facing surface of the increased diameter member may comprise a partial conic surface.

In some embodiments, which may be used in conjunction with any of the preceding aspects and embodiments, the expandable member may comprise a hollow cylindrical portion.

Other aspects of the present disclosure pertain to medical delivery systems that comprise: (a) a delivery device in accordance with any of the preceding aspects and embodiments and (b) an implantable device comprising an engagement region, wherein the expandable member is insertable into the engagement region, wherein the expandable member is slidable within the engagement region when in the relaxed state, and wherein the expandable member is configured to laterally expand to engage with the engagement region when in the expanded state.

In some embodiments of the preceding aspects, the engagement region may comprise an engagement region lumen having an engagement region lumen width that is greater than the first lateral width and less than or equal to the second width, such that the expandable member is slidable within the engagement region lumen when in the relaxed state and such that the expandable member engages the engagement region lumen when in the expanded state.

In some embodiments, which may be used in conjunction with any of the preceding aspects and embodiments, the engagement region may correspond to a portion of the implantable device or the engagement region may correspond to a separate engagement portion that is attached to the implantable device.

In some embodiments, which may be used in conjunction with any of the preceding aspects and embodiments, the implantable device may comprise a vascular occlusion device.

Other aspects of the present disclosure pertain to methods of implanting an implantable device in a subject comprising (a) inserting a medical delivery system in accordance with any of the preceding aspects and embodiments into a subject while exerting a pulling force on the second elongate member relative to the first elongate member when the expandable member is positioned within the engagement region such that the delivery device and implantable device are maintained in a coupled state and (b) releasing the pulling force, and optionally exerting a pushing force on the second elongate member relative to the first elongate member, such that the expandable member contracts in lateral width, thereby releasing the implantable device in the subject.

Other aspects of the present disclosure pertain to delivery devices for delivering detachable medical devices that comprise: (a) a first elongate member having a first elongate member lumen, (b) a second elongate member, and (c) an expandable member having an expandable member lumen a first lateral width when in a relaxed state. The second elongate member is at least partially positioned within the first elongate member lumen and the expandable member lumen, and a proximal end of the expandable member is attached to the first elongate member and a distal end of the expandable member is attached to the second elongate member such that a twisting movement between the inner elongate member and the outer elongate member causes the expandable member to expand from a relaxed state to an outwardly expanded state.

In some embodiments of the preceding aspects, the first elongate member may comprise a hollow cylindrical region having a lumen with a substantially circular cross-section.

In some embodiments, which may be used in conjunction with any of the preceding aspects and embodiments, the second elongate member may comprise a solid or hollow cylindrical region having a substantially circular cross-section.

In some embodiments, which may be used in conjunction with any of the preceding aspects and embodiments, when the increased diameter member is in an unexpanded state, the increased diameter member may have a width that is approximately equal to the first lateral width.

In some embodiments, which may be used in conjunction with any of the preceding aspects and embodiments, the increased diameter member may have a substantially circular cross-section.

In some embodiments, which may be used in conjunction with any of the preceding aspects and embodiments, the expandable member may comprise a hollow cylindrical portion.

Other aspects of the present disclosure pertain to medical delivery systems that comprise: (a) a delivery device in accordance with any the preceding aspects and (b) an implantable device comprising an engagement region, wherein the expandable member is insertable into the engagement region, wherein the expandable member is slidable within the engagement region when in the relaxed state, and wherein the expandable member is configured to laterally expand to engage with the engagement region when in the expanded state.

In some embodiments of the preceding aspects, the engagement region may comprise an engagement region lumen having an engagement region lumen width that is greater than the first lateral width and less than or equal to the second width, such that the expandable member is slidable within the engagement region lumen when in the relaxed state and such that the expandable member engages the engagement region lumen when in the expanded state.

In some embodiments, which may be used in conjunction with any of the preceding aspects and embodiments, the engagement region may correspond to a portion of the implantable device or the engagement region may correspond to a separate engagement portion that is attached to the implantable device.

In some embodiments, which may be used in conjunction with any of the preceding aspects and embodiments, the implantable device may comprise a vascular occlusion device.

Other aspects of the present disclosure pertain to methods of implanting an implantable device in a subject that comprise (a) inserting a medical delivery system in accordance with the preceding aspects into a subject while exerting a twisting force on the second elongate member relative to the first elongate member when the expandable member is positioned within the engagement region such that the delivery device and implantable device are maintained in a coupled state and (b) releasing the twisting force on the second elongate member relative to the first elongate member, such that the expandable member contracts in lateral width, thereby releasing the implantable device in the subject.

An advantage of the present disclosure is that improved devices, systems and methods for coupling and releasing implantable devices are provided.

These and other aspects, embodiments and advantages of the present disclosure will become immediately apparent to those of ordinary skill in the art upon review of the detailed description and claims to follow.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure. In the figures.

DETAILED DESCRIPTION

A more complete understanding of the present disclosure is available by reference to the following detailed description of numerous aspects and embodiments of the disclosure. The detailed description which follows is intended to illustrate but not limit the disclosure.

As used herein, the terms "proximal" and "distal" generally refer to the relative position, orientation, or direction of an element or action, from the perspective of a clinician using the medical device, relative to one another. Thus, "proximal" may generally be considered closer to the clinician or an exterior of a patient, and "distal" may generally be considered to be farther away from the clinician, along the length or beyond the end of the medical device.

Disclosed herein are delivery devices, systems and methods for delivering an implantable device to a target site, in particular, a detachable, implantable device. The systems include a delivery device that can temporarily hold an implantable device in a coupled arrangement by lateral expansion of an expandable member associated with the delivery device (e.g., by compression, displacement, twisting motion, etc.), within a proximal portion of the implantable device.

Figure 1A:
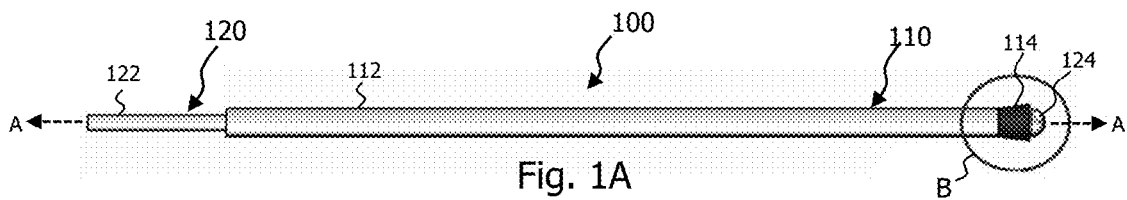
FIG. 1A is a schematic illustration of a delivery device in an expanded configuration in accordance with an embodiment of the present disclosure.
Figure 1B:
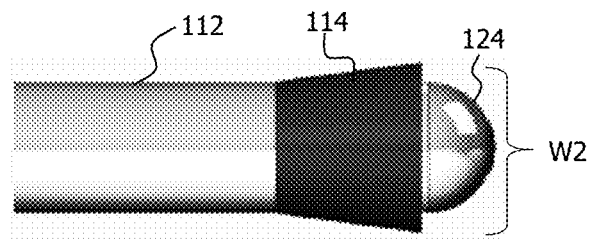
FIG. 1B is an expanded view of a distal portion of the delivery device of FIG. 1A.

Turning now to FIGS. 1A and 1B, these drawings illustrate a delivery device 100 suitable for delivering a detachable medical implant into a subject, in accordance with the present disclosure. FIG. 1B is an enlarged view of the distal portion of the delivery device 100, indicated by the encircled region B in FIG. 1A. The delivery device 100 has an axis A and comprises and a first delivery mechanism 110 comprising an outer elongate member 112 (also referred to herein as a first elongate member) and an expandable member 114 positioned distal to the outer elongate member 112. The expandable member 114 is mechanically linked to the outer elongate member 112 in the embodiment shown (e.g., by bonding, reflowing, or any other suitable method of attachment), but this is not required, as seen further below. The delivery device 100 further comprises a second delivery mechanism 120 comprising an inner elongate member 122 (also referred to herein as a second elongate member) and an increased diameter member 124 positioned distal to the inner elongate member 122. (As used herein, the term "lateral" or "laterally" is with regard to the axis A of the device.) The increased diameter member 124 may be, for example, with a substantially circular cross-section as shown, among others. The increased diameter member 124 is mechanically linked to the inner elongate member 122. In some embodiments, the increased diameter member 124 may be in the form of an enlarged tip of the inner elongate member. The inner elongate member 122 and the increased diameter member 124 may be formed of different materials or of the same material, in which case the inner elongate member 122 and the increased diameter member 124 may be formed of a unitary construction, if so desired.

Figure 2:
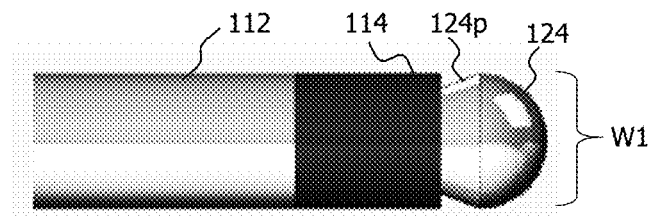
FIG. 2 is a schematic illustration of a distal portion of the delivery device of FIG. 1A when in a low-profile configuration.

The outer elongate member 112 may be, for example, in the form of a tube in the embodiment shown. The inner elongate member 122 may be, for example, in the form of a rod or a tube in the embodiment shown. The expandable member 114 has a lumen and a first overall width W1 when in a relaxed (unstressed) state as shown in FIG. 2. The inner elongate member 122 is disposed at least partially within respective lumens of the outer elongate member 112 and expandable member 114 in the embodiment shown, and is axially moveable relative to the outer elongate member 112 and expandable member 114. The increased diameter member 124 comprises a proximal facing surface 124p, as shown in FIG. 2. As a result, when the inner elongate member 122 is subjected to a proximal pulling force relative to the outer elongate member 112, the proximal facing surface 124p of the increased diameter member 124 engages the expandable member 114 (this can be seen by comparing FIG. 2 and FIG. 1B). As force is applied to the expandable member 114, the expandable member 114 expands in width from a relaxed state having a first width W1 to an outwardly expanded state having a second width W2 (see FIG. 1B) which is greater than the first width W1 Please add some numerical relationship between W1 and W2. For example, W2 may be at least about 1%, at least about 5%, at least about 10%, at least about 20% or at least about 30% greater than W1.

This outward expansion can be used to engage another device, for example, an implantable medical device such as a vascular occlusion device. For example, referring now to FIG. 3A, the distal end of a delivery device 100 like that illustrated in FIGS. 1A, 1B, and 2 is shown adjacent to a proximal end of a coil 200 such as an occlusion coil. In the embodiment shown in FIG. 3A, the expandable member 114 is in a relaxed state (as shown in FIG. 2) and the distal end of a delivery device 100 is of sufficiently narrow width such that it can be readily inserted into and/or retracted from the lumen defined by the coil 200. After insertion into the coil 200, the delivery device 100 engages the coil 200 by pulling the inner elongate member 122 proximally relative to the outer elongate member 112 such that the expandable member 114 expands in width and engages the interior of the coil 200 as shown in FIG. 3B. By maintaining a suitable amount of force between the inner elongate member 122 and the outer elongate member 112 (thus maintaining the inner elongate member 122 in tension and the outer elongate member 112 in compression), the delivery device 100 and coil 200 may be held in a coupled state. This allows the coil to be repositioned (for example, in order to ensure that coil "kickback" does not occur), or even allowing the coil to be withdrawn from the patient. Releasing the force between the inner elongate member and the outer elongate member, in some instances accompanied by a reversal in force by pushing the inner elongate member distally relative to the outer elongate member, allows the expandable member 114 to return to a smaller width state, thereby releasing the coil Multiple coils may be inserted and released in this fashion, if desired.

Figure 3A:
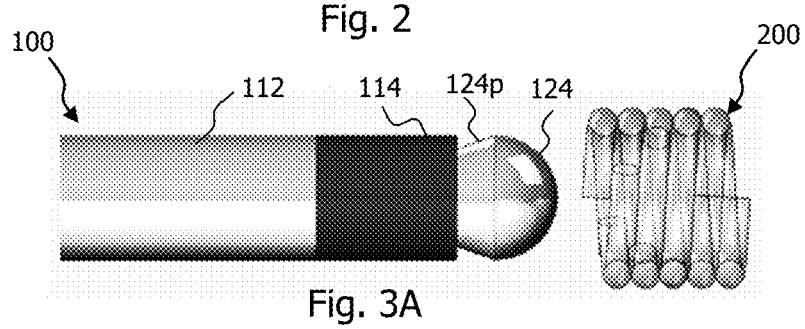
FIG. 3A is a schematic illustration of a distal portion of the delivery device of FIG. 1A when in a low-profile configuration adjacent to a proximal end of an embolic coil, in accordance with an embodiment of the present disclosure.
Figure 3B:
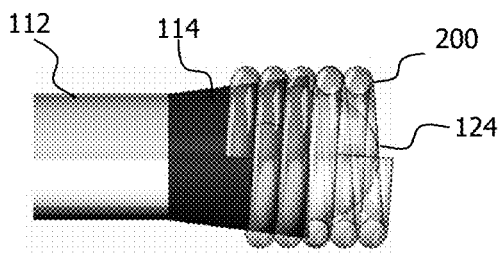
FIG. 3B is a schematic illustration of a distal portion of the delivery device of FIG. 1A disposed within and engaged with a proximal end of an embolic coil, in accordance with an embodiment of the present disclosure.
Figure 4:
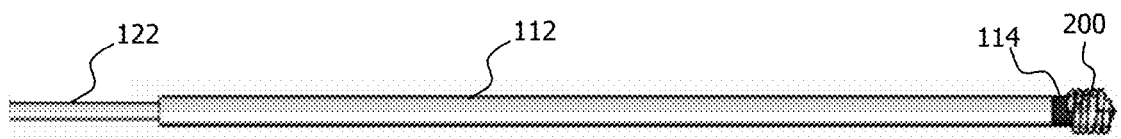
FIG. 4 is a schematic illustration of the delivery device of FIG. 1A disposed within and engaged with a proximal end of an embolic coil, in accordance with an embodiment of the present disclosure.
Figure 6:
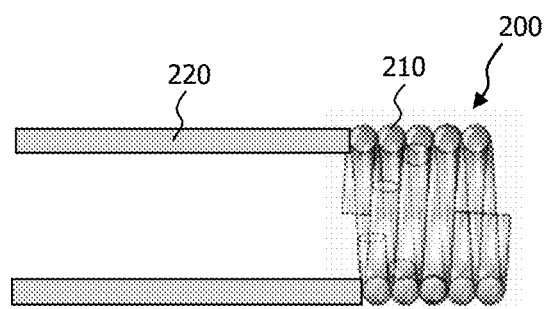
FIG. 6 is a schematic illustration of a proximal portion of coil having a coil portion and a cylindrical tether portion in accordance with another embodiment of the present disclosure.

In the embodiment shown in FIGS. 3A, 3B and 4, the medical device itself (e.g., the coil 200) provides an inner engagement surface for the expandable member 114. In other embodiments, a separate tether member having an engagement surface (e.g., a member having a region into which the expandable member may be inserted, expanded, and engaged) may be attached to a medical device. For instance, a hollow cylinder (e.g., a band or, in the case of a coil, a coil section) may be attached to (e.g., by welding or using a suitable adhesive) or co-formed with the medical device in order to provide a suitable lumen with an engagement surface. A coil 200 having a coil portion 210 and a cylindrical tether portion 220 is shown in FIG. 6 (in cross-section). A tether member may be beneficial, for example, where the geometry of the coil per se is not readily engaged by an expandable member (e.g., very small coils are deployed, etc.).

In various embodiments, the increased diameter member 124 has a width that is approximately equal to (e.g., within 10%, preferably within 5%, or even within 1%) of the width W1 of the expandable member 114 when in a relaxed state.

In various embodiments, the proximal facing surface 124*p* of the increased diameter member 124 is tapered such that engagement with and continued axial movement of the proximal facing surface 124*p* into the lumen of the expandable member 114 results in an outward force on the expandable member 114 (such as a laterally outward force, leading to outward lateral expansion of the expandable member 114, which progresses as the proximal facing surface 124*p* moves deeper into the lumen of the expandable member 114).

In the embodiment shown, proximal facing surface 124*p* is a partial conic surface, which provides a taper with a linear profile. In other embodiments, tapers with curved profiles may be provided, for example, by employing a partial spheroidal surface as the proximal facing surface 124*p*, among other possibilities.

Figure 5A:
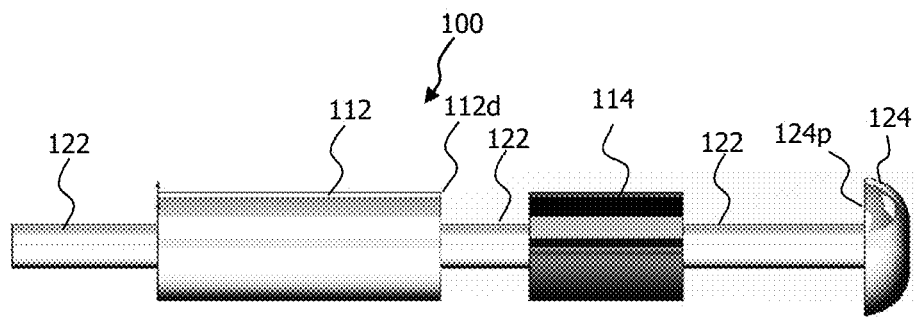
FIG. 5A is a schematic illustration of a distal end of a delivery device in accordance with another embodiment of the present disclosure.
Figure 5B:
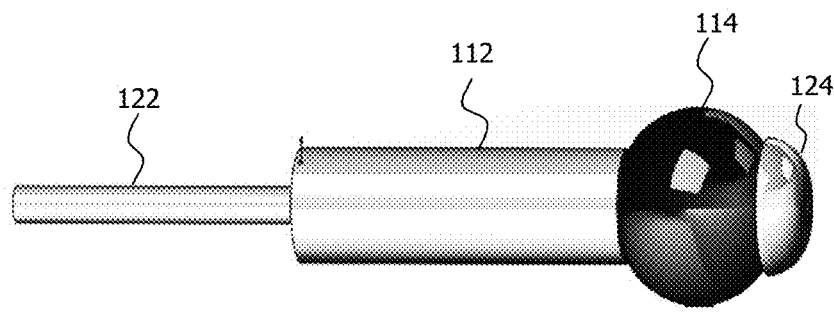
FIG. 5B is a schematic illustration of a distal portion of the delivery device of FIG. 5A, after activation of the device into an enlarged profile configuration.

In other embodiments, the proximal facing surface 124*p* of the increased diameter member 124 may be a blunt surface. For example, FIG. 5A illustrates a delivery device 100 suitable for delivering a detachable medical implant into a subject, in accordance with an embodiment of the present disclosure. The delivery device 100 comprises a first delivery mechanism comprising an outer elongate member 112 and an expandable member 114 disposed distal to a distal end of the outer elongate member 112. The expandable member 114 is not mechanically linked to the outer elongate member 112 in the embodiment shown, but may be so-attached as previously discussed. The delivery device 100 further comprises a second delivery mechanism comprising an inner elongate member 122 and an increased diameter member 124 (such as, an enlarged tip having a substantially circular outer surface) that is mechanically linked to the inner elongate member 122. The inner elongate member 122 is at least partially disposed within respective lumens of the outer elongate member 112 and expandable member 114 in the embodiment shown, and is axially moveable relative to the outer elongate member 112 and expandable member 114. The increased diameter member 124 comprises a flat proximal facing surface 124*p*, in this case, a disc-shaped flat proximal surface. When the inner elongate member 122 is pulled proximally relative to the outer elongate member 112, the proximal facing surface 124*p* of the increased diameter member 124 engages the expandable member 114 and presses it against the distal end 112*d* of the outer elongate member 112. As force is continued to be applied to the expandable member 114, the expandable member 114 expands from a relaxed state as shown in FIG. 5A to an outwardly expanded state as shown in FIG. 5B. Analogous to the device shown in FIGS. 1-4, this outward expansion can be used to temporarily engage another device.

In still other embodiments, the expandable member 114 is linked at its proximal end to the outer elongate member 112 and linked at its distal end to the inner elongate member 122 such that a twisting movement between the inner elongate member 122 and the outer elongate member 112 causes the expandable member 114 to expand from a relaxed state to an outwardly expanded state, which can be used to temporarily engage an engagement region of an implantable device.

As previously noted, the inner elongate member for use in various embodiments including those described herein is typically in the form of a solid elongate member (e.g., a solid rod, also referred to as a wire) or a tubular elongate member having a lumen, but more typically in the form of a solid elongate member. The outer elongate member for use in various embodiments including those described is typically in the form of a tubular elongate member having a lumen that is sized to accommodate at least a portion of the length of the inner elongate member.

In various embodiments, the expandable member may be, for example, in the shape of a hollow cylinder and thus of circular geometry; however, geometries including oval, helical, octagonal, hexagonal, toroidal and ribbed geometries may also be employed, among other possibilities.

As previously indicated, in accordance with various aspects of the present disclosure, medical systems are descried herein which comprise an implantable device and delivery device configured to reversibly engage and disengage the implantable device.

In certain embodiments, such a delivery system be employed to place one or more implantable device(s), including occlusion devices such as coils, plugs, tubes, and scaffolds, at a target site within the vasculature using a flexible, small diameter catheter. As a first step, the catheter may be guided to the target site through the use of a guidewire or by other means. Once the site has been reached, the catheter lumen is cleared by removing the guidewire (if a guidewire has been used) and the distal end of the system (such as, the distal end of the implantable device, which is engaged with the delivery device) is placed into a proximal open end of the catheter and advanced through the catheter via the delivery device.

During delivery, a force is maintained on the inner and outer elongate members such that the increased diameter member is pressed proximally against the expandable member (or the expandable member is pressed distally against the increased diameter member), maintaining the expandable member in an outwardly expanded state such that the medical device remains coupled to the delivery device. Once the implantable device emerges from the distal end of the catheter and is properly positioned at the targeted site, the force is discontinued (and optionally reversed), causing the increased diameter member to move distally relative to the expandable member, allowing the expandable member to contract. The resulting reduction in width causes the expandable member to disengage from the medical device, releasing the medical device at the target site.

As noted above, in some embodiments, the expandable member is linked at its proximal end to the outer elongate member and linked at its distal end to the inner elongate member such that a twisting movement between the inner elongate member and the outer elongate member causes the expandable member to expand from a relaxed state to an outwardly expanded state. In these embodiments, during delivery, a twisting force is exerted on the inner elongate member relative to the outer elongate, maintaining the expandable member in an outwardly expanded state such that the medical device remains coupled to the delivery device. Once the implantable device emerges from the distal end of the catheter and is properly positioned at the targeted site, the twisting force is discontinued, allowing the expandable member to contract. The resulting reduction in width causes the expandable member to disengage from the medical device, releasing the medical device at the target site.

As noted above, in certain embodiments, the medical device may comprise a vascular occlusion device, such as an embolic coil or other occlusion device. Where the medical device is an embolic coil, it may be formed from metals or alloys, for example, selected from platinum group metals, particularly platinum, rhodium, palladium, and rhenium, as well as tungsten, gold, silver, tantalum, and alloys of these metals including platinum/tungsten alloy. These materials have significant radiopacity, and their alloys may be tailored to have a blend of flexibility and stiffness for the coil. They are also generally biologically inert. The coil may also include shape memory components, such as nitinol components, among others.

The inner elongate member, outer elongate member, and increased diameter member may be formed using a variety of biocompatible materials. Beneficial materials for forming these objects include metals (including pure metals and metal alloys), for example, selected from stainless steel (e.g., 303, 304v, or 316L stainless steel), nickel-titanium alloy (nitinol) (e.g., super elastic or linear elastic nitinol), nickel-chromium alloy, nickel-chromium-iron alloy, cobalt alloy, nickel, titanium, platinum, and the like. Beneficial materials for forming the elongate delivery member further include stiff polymers such as polycarbonates, polyamides (e.g., nylons, etc.), parylene coatings or layers, and the like. In some embodiments, the elongate delivery member may be formed from a combination of polymeric and inorganic (e.g., metals, ceramics, etc.) materials.

Non-limiting examples of suitable materials for the expandable members described herein include natural and synthetic elastomers and mixtures thereof, including thermoplastic and thermosettable elastomers such as, for example, polysiloxane elastomers including polyalkysiloxane elastomers (e.g., crosslinked polydimethylsiloxane, also known as silicone rubber or silicone); thermoplastic polyurethanes including aromatic polyether-based thermoplastic polyurethanes such as Tecothane™; polyalkylene elastomers such as polyisobutylene elastomers, polyisoprene elastomers, polychloroprene elastomers, polybutadiene elastomers, ethylene-propylene elastomers and ethylene-butylene elastomers, specific examples of which include styrene-alkylene copolymers, including styrene-isobutylene copolymers such as styrene-isobutylene-styrene block copolymers, styrene-butadiene copolymers such as styrene-butadiene-styrene block copolymers; styrene-isoprene copolymers such as styrene-isoprene-styrene block copolymers, styrene-ethylene-butylene copolymers including styrene-ethylene-butylene-styrene block copolymers, styrene-ethylene-propylene copolymers including styrene-ethylene-propylene-styrene elastomers; nitrile rubbers (e.g., acrylonitrile-butadiene); butyl rubbers; ethylene-propylene-diene (EPDM) elastomers (EPDM); polypropylene-EPDM elastomers; ethylene vinyl acetate elastomers; polymethacrylate elastomers; polyacrylate elastomers including, for example, copolymers of isooctyl acrylate and acrylic acid; polyesters; polyether esters; polyvinyl chloride; polyvinylidene chloride; polyvinyl ethers; and blends thereof.

It will be appreciated that the various components of the disclosure including one or more of the inner elongate member, outer elongate member, expandable member, and increased diameter member, may be formed from or may include a radiopaque material. One skilled in the art will appreciate that a variety of imaging capable materials can be used, including, for example, materials detectable with, x-ray, including fluoroscopy, MRI, CT, PET, SPECT, and combinations thereof.

Although specific embodiments have been described with an embolic coil in the drawings, one of ordinary skill in the art will appreciate that variety of alternative medical devices could be substituted. For example, the systems described herein may be used to deliver a variety of implantable devices in addition, or as an alternative, to the embolic coil (e.g., scaffolding, drug-releasing devices, etc.).

Still further, while the delivery system is generally described with respect to the detachable device traveling through a catheter, one skilled in the art will appreciate that the device may travel through a variety of medical instruments, such as, for example, introducers or endoscopes, and that the methods and devices describe herein are equally applicable to any medical device having a lumen for the delivery of a detachable, implantable device. In this regard, the term "catheter" as used herein can refer to the variety of medical devices having an inner lumen adapted for receiving a medical instrument and/or implantable device.

Still other embodiments of the disclosure will be apparent to those skilled in the art from consideration of the specification and practice of the disclosure disclosed herein. It is intended that the specification and examples be considered as exemplary only.

What is claimed is:

1. A delivery device for delivering a detachable medical device comprising:
    (a) a first delivery mechanism comprising (i) a first elongate member having a first elongate member lumen and (ii) an expandable member having an expandable member lumen and a substantially planar continuous edge, the continuous edge having a first lateral width when in a relaxed state, said expandable member being positioned distal to said first elongate member; and
    (b) a second delivery mechanism comprising (i) a second elongate member and (ii) an increased diameter member having a proximal facing surf ace, said increased diameter member being positioned distal to and mechanically coupled to said first elongate member;
    wherein the second elongate member is at least partially positioned within the first elongate member lumen and the expandable member lumen, wherein the second elongate member is axially moveable relative to the first elongate member lumen and the expandable member lumen, and wherein the increased diameter member is positioned distal to the second elongate member such that when the second elongate member is pulled proximally relative to the first elongate member, the proximal facing surface of the increased diameter member compresses the expandable member by moving at least partially axially into the expandable member lumen such that the expandable member expands to an expanded state wherein the continuous edge has a second lateral width that is greater than the first lateral width.

2. The delivery device of claim 1, wherein the first elongate member comprises a hollow cylindrical region having a lumen with a substantially circular cross-section.

3. The delivery device of claim 1, wherein the second elongate member comprises a solid or hollow cylindrical region having a substantially circular cross-section.

4. The delivery device of claim 1, wherein said first elongate member is mechanically coupled to said expandable member.

5. The delivery device of claim 1, wherein said second elongate member and said increased diameter member are formed from different materials.

6. The delivery device of claim 1, wherein said second elongate member and said increased diameter member are formed from the same material and are of a unitary construction.

7. The delivery device of claim 1, wherein when the expandable member is in an unexpanded state, the increased diameter member has a width that is approximately equal to the first lateral width.

8. The delivery device of claim 1, wherein the increased diameter member has a substantially circular cross-section.

9. The delivery device of claim 1, wherein the proximal facing surface of the increased diameter member is a tapered surface.

10. The delivery device of claim 1, wherein the proximal facing surface of the increased diameter member comprises a partial conic surface.

11. The delivery device of claim 1, wherein the expandable member comprises a hollow cylindrical portion.

12. A medical delivery system comprising:
a delivery device comprising (a) a first delivery mechanism comprising (i) a first elongate member having a first elongate member lumen and (ii) an expandable member having an expandable member lumen and having a first lateral width when in a relaxed state, said expandable member being positioned distal to said first elongate member and (b) a second delivery mechanism comprising (i) a second elongate member and (ii) an increased diameter member having a proximal facing surface, said increased diameter member being positioned distal to and mechanically coupled to said second elongate member, wherein the second elongate member is at least partially positioned within the first elongate member lumen and the expandable member lumen, wherein the second elongate member is axially moveable relative to the first elongate member lumen and the expandable member lumen, and wherein the increased diameter member is positioned distal to the second elongate member such that when the second elongate member is pulled proximally relative to the first elongate member, the proximal facing surface of the increased diameter member engages a substantially planar continuous edge of the expandable member and expands the expandable member by moving at least partially axially into the expandable member lumen such that the expandable expands to an expanded state having a second lateral width that is greater than the first lateral width; and
an implantable device comprising an engagement region, wherein the expandable member is insertable into the engagement region, wherein the expandable member is slidable within the engagement region when in said relaxed state, and wherein the expandable member is configured to laterally expand to engage a proximal end of the implantable device with the engagement region when in said expanded state.

13. The medical delivery system of claim 12, wherein the engagement region corresponds to a portion of the implantable device or wherein the engagement region corresponds to a separate engagement portion that is attached to the implantable device.

14. The medical delivery system of claim 12, wherein the implantable device comprises a vascular occlusion device.

15. The medical delivery system of claim 12, wherein the engagement region comprises an engagement region lumen having an engagement region lumen width that is greater than the first lateral width and less than or equal to said second lateral width, such that the expandable member is slidable within the engagement region lumen when in said relaxed state and such that the expandable member engages the engagement region lumen when in said expanded state.

16. A method of implanting an implantable device in a subject, the method comprising:
inserting a medical delivery system in accordance with claim 15 into a subject while exerting a pulling force on the second elongate member relative to the first elongate member when the expandable member is positioned within the engagement region such that the delivery device and implantable device are maintained in a coupled state; and
releasing the pulling force, and optionally exerting a pushing force on the second elongate member relative to the first elongate member, such that the expandable member contracts in lateral width, thereby releasing the implantable device in said subject.

17. A delivery device for delivering a detachable medical device comprising:
(a) a first delivery mechanism comprising (i) a first elongate member having a first elongate member lumen and (ii) an expandable member having an expandable member lumen and having a first lateral width when in a relaxed state, said expandable member being positioned distal to said first elongate member; and
(b) a second delivery mechanism comprising (i) a second elongate member and (ii) an increased diameter member having a proximal facing surface, said increased diameter member being positioned distal to and mechanically coupled to said second elongate member;
wherein the second elongate member is at least partially positioned within the first elongate member lumen and the expandable member lumen, wherein the second elongate member is axially moveable relative to the first elongate member lumen and the expandable member lumen, and wherein the increased diameter member is positioned distal to the second elongate member such that when the second elongate member is pulled proximally relative to the first elongate member, the proximal facing surface of the increased diameter member compresses the expandable member by moving at least partially axially into the expandable member lumen such that the expandable member expands to an expanded state wherein the expandable member has a second lateral width that is greater than the first lateral width; and
an implantable device comprising an engagement region, wherein the expandable member is insertable into the engagement region, wherein the expandable member is slidable within the engagement region when in said relaxed state, and wherein the expandable member is configured to laterally expand to engage a proximal end of the implantable device with the engagement region when in said expanded state.

18. The delivery device of claim 17, wherein the first elongate member comprises a hollow cylindrical region having a lumen with a substantially circular cross-section.

19. The delivery device of claim 17, wherein the second elongate member comprises a solid or hollow cylindrical region having a substantially circular cross-section.

\* \* \* \* \*